United States Patent [19]

Lam et al.

[11] 4,158,546

[45] Jun. 19, 1979

[54] COMPOSITION, TEST DEVICE AND METHOD FOR DETERMINING THE PRESENCE OF UROBILINOGEN IN A TEST SAMPLE

[75] Inventors: Charles T. W. Lam; Chauncey O. Rupe, both of Elkhart, Ind.

[73] Assignee: Miles Laboratories, Inc., Elkhart, Ind.

[21] Appl. No.: 927,517

[22] Filed: Jul. 24, 1978

[51] Int. Cl.² ............... G01N 21/06; G01N 33/16
[52] U.S. Cl. .................. 23/230 B; 252/408; 422/56
[58] Field of Search .......... 23/230 B, 253 TP; 252/408

[56] References Cited

U.S. PATENT DOCUMENTS

| | | | |
|---|---|---|---|
| 3,850,576 | 11/1974 | Rittersdorf | 23/230 B |
| 3,853,466 | 12/1974 | Rittersdorf | 23/230 B |
| 3,989,462 | 11/1976 | Hirsch | 23/230 B |
| 4,038,485 | 7/1977 | Johnston | 23/253 TP X |

*Primary Examiner*—Sidney Marantz
*Attorney, Agent, or Firm*—Edward H. Gorman, Jr.

[57] ABSTRACT

A novel test composition, device and method for determining the presence of urobilinogen in a test sample. The composition is capable of producing a detectable response, such as a change in color or change in light absorption, thus indicating the presence of urobilinogen, both on a qualitative and a semi-quantitative basis. Briefly, the composition comprises para-di(lower alkyl) aminobenzaldehyde as an indicator compound, a buffer substance capable of producing a pH of about 0.5 to 3, and a compound having the structure

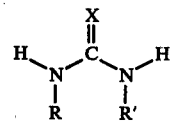

in which X is O or S, and in which R and R', same or different, are lower alkyl, or R and R' together are lower alkylene or

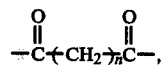

wherein n is an integer of 1 to about 6. The device comprises a carrier matrix incorporated with the composition. The method of use comprises contacting a test sample with the composition or device and observing any detectable response formed therein.

20 Claims, No Drawings

COMPOSITION, TEST DEVICE AND METHOD FOR DETERMINING THE PRESENCE OF UROBILINOGEN IN A TEST SAMPLE

BACKGROUND OF THE INVENTION

1. Field of the Invention

The present invention relates to the detection of urobilinogen in a test sample. More particularly, it relates to an improved test composition, device and method for detecting urobilinogen.

2. Description of the Prior Art

The analysis of urobilinogen species in urine is an old art which had its beginning around the turn of the century (1901) when Ehrlich discovered that p-dimethylaminobenzaldehyde reacts with urobilinogen in the presence of strong acid such as HCl to give a red color. This reaction was concurrently discovered by Proescher in the same year, and hence, the test is interchangeably referred to as the "Ehrlich" or "Ehrlich-Proescher" reaction. The chemistry underlying these simultaneous discoveries still forms the basis of today's urobilinogen testing.

This extensive utility and wide acceptance in medical diagnostics notwithstanding, it was soon found that the basic Ehrlich reaction is susceptible to various interfering substances in urine. Specifically, it was found that indole and skatole derivatives, pyrrole compounds, sulfonamides, and other substances interfered with the reaction by generating the red color typical of a positive test result. In 1925 Terwen found that by adding sodium acetate not only was the urobilinogenaldehyde color intensified, but also the color due to indole and skatole derivatives was inhibited. Modifications of this improvement are still in use as evidenced by U.S. Pat. No. 3,447,905. More recently, attempts to provide additional diagnostic agents for use in urobilinogen detection have resulted in systems such as that disclosed in U.S. Pat. No. 3,630,680. To date, the significant urobilinogen tests which have been developed rely almost exclusively on the use of p-dialkylaminobenzaldehyde indicators such as p-dimethylaminobenzaldehyde. Such a product is currently marketed by the Ames Division of Miles Laboratories, Inc. as UROBILISTIX® reagent strips.

The present invention departs from the state of the art in that it is directed to a unique improvement in the Ehrlich reaction. The new composition provides shorter reaction time, more intense color formation and less interference by such urine constituents as nitrite, isonicotinic acid hydrazide, p-aminosalicylic acid and indole.

Moreover, the use of the presently claimed composition in preparing test devices for measuring urobilinogen results in a greatly simplified procedure. Prior to the present invention, so-called "dip-and-read" reagent strips for urobilinogen were prepared by a two-dip process. Thus, a first reagent solution was prepared by dissolving aminoacetic acid and fluoboric acid in an alcoholic water solvent. This first solution was used to impregnate a carrier matrix, for example paper, which was then dried. A second reagent solution was then prepared containing a stannic chloride dioxane complex and p-dimethylaminobenzaldehyde in methanol. The dried impregnated paper was then immersed into this second solution and dried.

Surprisingly, because of the resultant enhanced stability of the presently claimed reagent system, test devices can be prepared using only a single impregnation or one-dip method. Because of the unexpected stability of the present composition, all of the ingredients can be dissolved in a single reagent solution, thus eliminating the costly, cumbersome second dip.

Another advantage of the present invention is that it eliminates the need for the highly acidic components of prior art devices which caused degradation of paper carrier matrices. The present state of the art requires the use of such compounds as $SnCl_4$ dioxane complex as a source of HCl in the reaction. Because of the relatively high reactivity of this component with paper in the presence of water, the two-dip preparation is necessary, the first dip to properly buffer and prepare the carrier matrix for the acid-producing complex. The present invention obviates the necessity of such a first step. The finished product utilizing the present composition enables a faster reaction time with the development of a much more intense color (yellow to deep red) than was heretofore available. In addition, the color range that is developed in the present invention is broader than that of the prior art, thereby enabling the use of more color blocks than prior art techniques over an equivalent range of urobilinogen levels.

To summarize the advantages of the present invention over the prior art, the rate of reaction is enhanced so that the waiting period for color development or other detectable response is greatly diminished; the color formed in the reaction is of much greater intensity than that of the prior art, thus facilitating greater sensitivity and accuracy; and a one-dip process can be used to manufacture the device as opposed to the two-dip process required in manufacturing the prior art reagent strips.

SUMMARY OF THE INVENTION

Briefly stated, the present invention relates to a composition, test device, and method of using the composition or device for determining the presence of urobilinogen in a test sample. The composition is one capable of producing a detectable response in the presence of urobilinogen and comprises para-di(lower alkyl)aminobenzaldehyde as an indicator compound, a buffer substance capable of producing a pH of about 0.5 to 3, and a compound having the structure

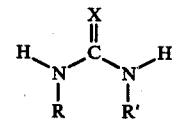

in which X is O or S, and in which R and R', same or different, are lower alkyl, or R and R' together are lower alkylene or

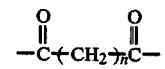

in which n is an integer from 1 to about 6. The test device claimed herein comprises a carrier matrix incorporated with the composition. The method comprises contacting the composition or test device with a test sample suspected of containing urobilinogen and observing any detectable response.

DETAILED DESCRIPTION OF THE INVENTION

The composition of the present invention embodies three principal components: an indicator, a buffer, and a compound derived from urea in which both amido-nitrogen atoms are substituted so as to be acyclic or cyclic. The indicator compound is selected from various para-di(lower alkyl)aminobenzaldehydes. These compounds are the familiar Ehrlich's reagent indicators and include p-dimethylaminobenzaldehyde, p-diethylaminobenzaldehyde, p-diisopropylaminobenzaldehyde, and other similarly substituted p-aminobenzaldehydes in which the lower alkyl group has from 1 to about 6 carbon atoms.

The buffering substance used in this composition is one capable of producing a pH of about 0.5 to 3. Thus, when the composition per se is used for analyzing a sample, it should have a pH falling in this range. Likewise, if the composition is used in the form of a reagent strip test device, the buffer used should provide a pH of about 0.5 to 3 upon wetting of the carrier matrix. Some examples of buffers which are compatible with the present invention are sulfosalicylic acid, hexamic acid, oxalic acid, and phosphoric acid.

The third principal ingredient of the composition comprises a compound having the structure

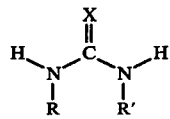

in which X is O or S, and R and R' can be a lower alkyl group, such as methyl, ethyl, isopropyl, n-propyl, various butyl isomers and others, and can have up to about 6 carbon atoms. R and R' can also together form a lower alkylene group having 1 to about 6 carbon atoms, such as methylene or ethylene, or

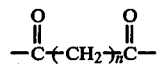

in which n is an integer from 1 to about 6 thereby producing a closed ring system. Examples of suitable compounds fulfilling these requirements are urea, 2-imidazolidone, malonyl urea, malonyl thiourea, and uric acid.

The compositions of the present invention can include, in addition to the above three principal ingredients, numerous ancillary components. For example, the formulation can include such diverse compounds as triethanolamine borate, caffeine, ascorbic acid and other formulation ingredients. Thus, it has been found that the effects of nitrite inhibition can be significantly abated by including ascorbic acid in the formulation. The sensitivity and reaction rate of the basic Ehrlich formulation can be further increased by the presence of caffeine. Triethanolamine borate significantly enhances the stability of the composition during both its formulation and shelf life. Other, art-recognized ingredients, such as surfactants and chelating agents, can be used to assist in solubilizing the components of the dip solution and to reduce other adverse effects. Accordingly, the present invention includes urobilinogen-sensitive reagent formulations comprising the three principal ingredients stated above with or without other ancillary components.

The amount of each of the principal ingredients of the urobilinogen-sensitive formulation can vary widely. Thus, the indicator can be present in a range of about 0.001 to about 5.0 weight percent; the buffer in a range of about 1 to about 20 weight percent, and the urea derivative or third ingredient in a range of about 0.001 to about 20 weight percent; based on total ingredients of the composition.

The test device of the present invention comprises a carrier matrix incorporated with the abovementioned test composition. The carrier matrix can take many forms. For example, U.S. Pat. No. 3,846,247 teaches the use of felt, porous ceramic strips, and woven or matted glass fibers. As substitutes for paper, U.S. Pat. No. 3,552,928 teaches the use of wood sticks, cloth, sponge material, and argillaceous substances. The use of synthetic resin fleeces and glass fiber felts in place of paper is suggested in British Pat. No. 1,369,139. Another British Pat. No. 1,349,623, suggests the use of a light-permeable meshwork of thin filaments as a cover for an underlying paper matrix. This reference also suggests impregnating the paper with part of the reagent system and impregnating the meshwork with other potentially incompatible reagents. French Pat. No. 2,170,397 teaches the use of carrier matrices having greater than 50% polyamide fibers therein. Another approach to carrier matrices is disclosed in U.S. Pat. No. 4,046,513 wherein the concept of printing reagents onto a suitable carrier matrix is employed. U.S. Pat. No. 4,046,514 discloses the interweaving or knitting of filaments bearing reagents in a reactant system. All such carrier matrix concepts can be employed in the present invention, as can others.

The preferred method of preparation of the presently claimed test device embodies a multitude of steps beginning wth the impregnation of a continuous roll of filter paper carrier matrix material by immersing the paper into a reagent bath containing the urobilinogen-sensitive reagent system. After drying, the paper is laminated to a continuous plastic sheet of a backing material such as a transparent polystyrene film known as Trycite ® (Dow Chemical Co.). The preferred method for attaching the impregnated carrier matrix to the plastic is through the use of an intermediate application of double-faced adhesive tape. Such tape is commercially marketed by 3M Company under the trademark Double Stick. When the impregnated filter paper has been applied to the backing material, the composite is cut so that the finished product is an elongated plastic strip having a rectangular section of impregnated carrier matrix laminated to a portion of one end thereof, the balance of the plastic serving as a handle.

In the method for using the presently claimed test device, the carrier matrix containing the urobilinogen-responsive composition is momentarily immersed into the test sample and withdrawn. After removal from the test sample, the composition incorporated with the carrier matrix is permitted to develop color or otherwise exhibit a detectable response, and is then observed. Methods of observing the response in or on the matrix include measuring the amount of light absorbed, both before and after immersion using a spectrophotometer or other appropriate device, or visually comparing any color change in the carrier matrix with standard color blocks corresponding to predetermined urobilinogen levels.

The following examples are provided to portray in detail the various steps of making and using the present invention. The examples are meant to be illustrative only, and should not be interpreted as in any way limiting the scope of the present invention.

EXAMPLES

A. Preparing the Composition and Test Device

EXAMPLE 1

The Composition with 2-imidazolidone

A Composition sensitive to urobilinogen was prepared from the following ingredients:

| | |
|---|---|
| sulfosalicylic acid | 520.0 grams (g) |
| p-dimethylaminobenzaldehyde | 40.0 g |
| triethanolamine borate | 80.0 g |
| 2-imidazolidone | 160.0 g |
| caffeine | 320.0 g |
| Versene ® (Dow Chemical Co.) | 8.0 g |
| ascorbic acid | 200.0 g |
| F,D & C blue solution* | 4.0 milliliters (ml) |

*Prepared by dissolving 20.0 milligrams F,D & C Blue No. 1 in 4.0 milliliters distilled water The composition was prepared by dissolving the above ingredients, in the order shown, in four liters of distilled water. Care was taken to assure that each ingredient was completely dissolved before the next one was added. The resultant solution develops a bright yellow green color, and turns varying shades of red in the presence of varying amounts of urobilinogen.

EXAMPLE 2

The Test Device with 2-imidazolidone

A bath was prepared containing the solution of Example 1 and was used to impregnate approximately 230 feet of filter paper from an eight inch roll (Eaton and Dikeman 237 filter paper). After the filter paper had passed through the bath, it was dried at a temperature of about 80°–82° C. in an air tunnel for about 15 minutes. To one side of the dry impregnated paper was applied a layer of adhesive tape known under the trademark Double Stick, the remaining exposed side of the adhesive tape being protected by a non-adhesive paper capable of being easily pulled away from the adhesive. The impregnated paper with its adhesive tape now attached was slit into ribbons of approximately 5 millimeters in width. The resulting ribbons were then applied to one side of a plastic Trycite ® ribbon approximately 70 millimeters in width. This was accomplished by stripping away the non-adhesive protective paper from the adhesive tape and pressing the exposed adhesive tape against the Trycite. The Trycite ribbon containing the mounted impregnated paper ribbon was then cut in a direction perpendicular to its length into strips measuring 5 millimeters wide. This resulted in a series of urobilinogen-sensitive test strips measuring 5 by 70 millimeters, and containing a urobilinogen-sensitive reagent area measuring 5 by 5 millimeters at one end of the strip. This resulted in a urobilinogen test device sensitive to one Ehrlich unit of urobilinogen per deciliter of urine.

EXAMPLE 3

The Composition and Test Device with Malonyl Urea

A bath was prepared containing the following ingredients:

| | | |
|---|---|---|
| distilled water | 80.0 | milliliters (ml) |
| tetrahydrofuran | 20.0 | ml |
| sulfosalicylic acid | 11.6 | grams (g) |
| p-diethylaminobenzaldehyde | 0.048 | g |
| malonyl urea | 0.16 | g |
| triethanolamine borate | 1.8 | g |
| caffeine | 9.7 | g |
| Versene | 0.18 | g |
| ascorbic acid | 4.4 | g |

The tetrahydrofuran and distilled water were mixed and the solid components added in the order given above, each component in turn being completely dissolved before addition of the next. The resulting light orange colored solution was stirred for about 30 minutes.

Strips of Eaton and Dikeman No. 237 filter paper were impregnated with the solution and dried in a hot air oven at 80° C. for 15 minutes to provide test devices of the present invention which had a light orange color. Sections of the impregnated paper devices were mounted on Trycite ® (Dow Chemical Co.) using 3M Company's Double Stick adhesive as described in Example 2.

EXAMPLE 4

The Composition and Test Device with a 2-Thiomalonyl Urea

A bath was prepared containing the following ingredients:

| | | |
|---|---|---|
| 50% aqueous methanol solution | 15 | ml |
| sulfosalicylic acid | 3 | gm |
| p-dimethylaminobenzaldehyde | 4.8 | mg |
| 2-thiomalonyl urea | 4.8 | mg |
| caffeine | 400 | mg |
| 50% aqueous methanol to make | 20 | ml |

The solid components were sequentially added to the aqueous methanol in the order listed. After addition of solids, the solution was brought to 20 ml volume by further addition of aqueous methanol.

Strips of Eaton and Dikeman No. 237 filter paper were impregnated with this solution and dried in a hot air oven at about 75°–80° C. to provide test devices.

EXAMPLE 5

Control Test Device

A test device is prepared as a control for use in assessing the improved characteristics of the present invention. It is made following the two-dip process of the prior art.

A first dip is prepared by combining the following ingredients:

| | |
|---|---|
| ethanol | 42.6 milliliters |
| dioctyl sodium sulfosuccinate | 425.5 milligrams |
| distilled water | 1.0 liter |
| glycine | 106.4 grams |
| fluoboric acid | 23.4 ml |

The ingredients are combined by first mixing the dioctyl sodium sulfosuccinate in the ethanol with stirring until dissolved. The distilled water is placed in a separate container and the glycine added with stirring until dissolved. To this aqueous solution is added the ethanolic dioctyl sodium sulfosuccinate solution. To this mixture is added the fluoboric acid with stirring.

Through this solution is passed a strip of filter paper (Eaton and Dikeman 237), which is then dried at about 80°–100° C. in an air tunnel for about 15 minutes.

A second dip solution is prepared by combining the following ingredients:

| | |
|---|---|
| methanol | 1.0 liter |
| tris(hydroxymethyl)aminomethane | 12.5 grams |
| stannic chloride dioxane (Sumner Division, Miles Laboratories, Inc.) | 375 grams |
| p-dimethylaminobenzaldehyde | 15.6 grams |

These are mixed by adding to the methanol each of the other three ingredients, with stirring, in the order in which they are listed.

Through this solution is passed the impregnated paper from the first dip. The paper exiting the second dip is then dried at about 80° to 100° C. in the drying tunnel.

Upon drying, the impregnated paper is applied to one side of double-faced adhesive tape obtained from 3M Company. The remaining adhesive side is contacted with a sheet of Trycite ® (Dow Chemical Co., Inc.). The impregnated paper/adhesive tape/Trycite composite is then cut into strips measuring 4 inches by 0.2 inches. The impregnated paper portion measures 0.2 by 0.2 inches.

B. Evaluation of Test Devices

EXAMPLE 6

"Blind Study" Data Accumulation Procedure

Blind studies were conducted to provide comparison data for the test device of Example 2 and the prior art (control device of Example 5). In these studies, groups of five or more people dipped reagent strips into urine samples and estimated the urobilinogen content of the sample by comparing any color developed in the strip with standardized color blocks.

The color blocks were assigned arbitrary numerical values from 0 to 30. Thus the color block indicative of 0.1 Ehrlich Units urobilinogen per deciliter of urine (E.U./dl.) was assigned an arbitrary value of 0. A second block was the color of the reagent strip at 1 E.U./dl. urobilinogen and was assigned the value of 10. A third color block, assigned a value of 20, corresponded to the reagent strip color in urine containing urobilinogen at a concentration of 2 E.U./dl. Finally, the color block for 4 E.U./dl. urobilinogen concentration was assigned the value of 30. Where the color of the reagent strip fell between two color blocks, interpolative values were assigned. The readings for a particular reagent strip with a particular urine sample were averaged in accordance with the number of persons making each reading in order to eliminate, as much as possible, subjectiveness in personal color interpretation.

The above-described blind study procedure was employed to assess the effects of various urine parameters on the efficacy of test devices from Example 2 and the control, or prior art, devices of Example 5. Those parameters observed were nitrite, isonicotinic acid hydrazide, p-aminosalicylic acid, and indole.

EXAMPLE 7

The Effect of Nitrite

A blind study as described in Example 6 was performed to assess the relative effects of nitrite ion in urine on urobilinogen analysis using test devices of the present invention (Example 2) and those of the prior art (control strips of Example 5).

Four color blocks were prepared as references to color formation in each of the two types of reagent strips. Thus, color reference blocks corresponding to urobilinogen levels of 0.1, 1.0, 2 and 4 E.U./dl were prepared for each strip type and each block was assigned an arbitrary numerical value of 0, 10, 20 and 30, respectively.

Samples of pooled urine were prepared and urobilinogen was added to produce concentrations of 1.0, 2.0 and 4.0 E.U./dl. To these samples varying amounts of nitrite were added, and the two types of test strips were dipped in each solution. The color changes observed were assigned numerical values based on the standard color blocks. The results are recorded in Table I.

TABLE I

| The Effect of Nitrite on Urobilinogen Determination | | | | | | |
|---|---|---|---|---|---|---|
| | UROBILINOGEN CONCENTRATION (E.U./dl) | | | | | |
| | 1.0 | | 2.0 | | 4.0 | |
| $NO_2$ (mg/dl) | Ex.2 | Ex.5 | Ex.2 | Ex.5 | Ex.2 | Ex.5 |
| .1 | 10.8 | 3.4 | 19.6 | 8.2 | 29.4 | 10.0 |
| .2 | 10.0 | 6.2 | 15.0 | 5.4 | 28.0 | 8.2 |
| .3 | 9.6 | 1.0 | 17.6 | 1.2 | 25.0 | 4.8 |
| .5 | 8.0 | 1.8 | 12.0 | 2.4 | 22.4 | 6.2 |
| .6 | | | 12.2 | 2.4 | 20.0 | 5.6 |
| .8 | | | 13.0 | 2.6 | 18.0 | 5.4 |
| 1.0 | | | 10.4 | 3.6 | 22.0 | 4.0 |
| Expected Value | 10 | 10 | 20 | 20 | 30 | 30 |

The data shows that nitrite has a profound effect on prior art urobilinogen test devices, whereas the effect is greatly diminished in those of the present invention. At a urobilinogen level of 1.0 E.U./dl. the control test strip read far below that of the present invention at a nitrite concentration of only 0.1 mg/dl., whereas the strip from Example 2 was unaffected (readings of 3.4 and 10.8, respectively). When nitrite was increased to 0.3 and 0.5, the present invention read as 9.6 and 8.0, very close to the value of 10.0 corresponding to the true urobilinogen level, whereas the control read only 1.0 and 1.8. Taking into consideration the effects of nitrite on the strips of Experiments 2 and 5, the present invention gave only slightly depressed values of actual urobilinogen, whereas the control gave falsely negative values (0.1 E.U./dl. compared with the actual concentration of 1.0 E.U./dl.).

When similar experiments were conducted with higher urobilinogen concentrations, the control was even more adversely effected, whereas the formulation of the present invention displayed far less interference from nitrite.

EXAMPLE 8

The Effect of Isonicotinic Acid Hydrazide

A blind study as described in Example 6 was performed to assess the relative effects of isonicotinic acid hydrazide (INH) in urine on urobilinogen test devices of the present invention (Example 2) and of the prior art (Example 5).

Color reference blocks were prepared as in Example 7 above for both reagent strip types corresponding to the same uro-bilinogen levels of 0.1, 1.0, 2.0 and 4.0. Again, arbitrary numerical values of 0, 10, 20 and 30, respectively, were assigned each color block for use in evaluating reagent strip performance.

Test samples were prepared using pooled normal urine to which varying amounts of INH were added. Since INH affects the standard Ehrlich reagent by giving a false positive result, this experiment was performed to test whether the present invention responds positively to the presence of INH in the test sample. The results are given in Table II.

TABLE II

| The Effect of INH on Urobilinogen Test Strips | | |
|---|---|---|
| INH | Color Response Values | |
| (mg./dl.) | Example 2 Strips | Example 5 Strips |
| 20 | 2.6 | 11.7 |
| 60 | 2.5 | 10.0 |
| 100 | 4.2 | 18.3 |
| 300 | 4.7 | 35.8 |
| 500 | 5.3 | 42.5 |
| 700 | 6.8 | 46.6 |

The data shows that INH levels of up to 700 mg/dl. did not produce seriously misleading results in the test device of Example 2 (the present invention), whereas the same concentrations produced readings in the prior art reagent strips equivalent to very high urobilinogen levels (46.6>3.0 E.U./dl. urobilinogen). Thus prior art strips are shown to be susceptible to INH interference to a much higher degree than are strips made in accordance with the present disclosure.

EXAMPLE 9

The Effects of p-Aminosalicylic acid

A blind study similar to that described in Example 6 was performed to assess the effects of the presence of p-aminosalicylic acid (PAS) in urine test samples on urobilinogen test devices of the present invention (Example 2) and those of the prior art (Example 5).

Color blocks were prepared as in Example 7 for assessing color development in the strips used in this experiment. Reagent strips from Examples 2 and 5 were dipped into pooled normal urine test samples to which had been added various amounts of PAS. No urobilinogen was added. A positive reading in a strip indicated a positive response to the presence of PAS, thus indicating that a probable falsely high reading would have been indicated, had urobilinogen been present in the urine sample. The results are given in Table III.

TABLE III

| The Effect of PAS on Urobilinogen Test Strips | | |
|---|---|---|
| PAS | Color Response Values | |
| (mg./dl.) | Example 2 Strips | Example 5 Strips |
| 0 | 8.3 | 4.2 |
| 20 | 16.0 | 25.0 |
| 40 | 16.0 | 28.0 |
| 60 | 19.7 | 39.0 |
| 80 | 26.0 | 37.0 |

The data indicates that, although some interference from PAS occurred in both sets of reagent strips, those of the prior art were far more susceptible.

EXAMPLE 10

The Effect of Indole

Experiments similar to those of Examples 7–9, above, were conducted to study the adverse effects of varying quantities of indole in the test sample on the ability of reagent strips from Examples 2 and 5 to determine urobilinogen levels in urine.

Pooled normal urine samples were charged with various amounts of indole. No urobilinogen was added. These urine samples were tested with test devices prepared as in Examples 2 and 5 and the results are given in Table IV.

TABLE IX

| The Effects of Indole on Urobilinogen Test Strips | | |
|---|---|---|
| Indole | Color Response Values | |
| (mg./dl.) | Example 2 Strips | Example 5 Strips |
| 0 | 0 | 3.0 |
| 1.0 | 0 | 10.0 |
| 2.0 | 2.0 | 24.0 |
| 3.0 | 6.6 | 30.0 |
| 4.0 | 5.0 | 37.0 |
| 5.0 | 12.0 | 42.0 |
| 6.0 | 12.0 | 44.0 |
| 7.0 | 11.2 | 42.0 |

The data indicates that the test device of the present invention suffered only negligible adverse effects from indole up to concentrations of 4.0 mg/dl. Prior art devices, however, were severely affected by similar amounts. Thus, a urobilinogen reading of 4.0 E.U./dl. occurred with the prior art strip when, in fact, no urobilinogen had been added. When indole was present in higher amounts (5–7 mg/dl. indole), the adverse effect of the indole was greatly diminished in devices of the present invention.

What is claimed is:

1. In a composition capable of producing a detectable response in the presence of urobilinogen in a test sample, which composition comprises p-di(lowr alkyl)aminobenzaldehyde as an indicator and a buffer substance capable of producing a pH of about 0.5 to 3, the improvement wherein said composition further comprises a compound having the structure

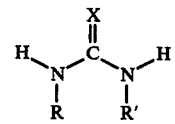

in which X is O or S; and in which R and R', same or different, are lower alkyl, or in which R and R' together are lower alkylene or

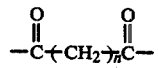

wherein n is an integer from 1 to about 6.

2. The improvement of claim 1 in which R and R' together form $-(CH_2)_n$, in which n is an integer of 1 to about 6.

3. The improvement of claim 1 in which said compound is 2-imidazolidone.

4. The improvement of claim 3 in which said indicator compound is p-dimethylaminobenzaldehyde.

5. The improvement of claim 1 in which said compound is malonyl urea.

6. The improvement of claim 5 in which said indicator is p-diethylaminobenzaldehyde.

7. A composition for determining the presence of urobilinogen in a test sample, the composition comprising 2-imidazolidone, p-dimethylaminobenzaldehyde, sulfosalicylic acid, triethanolamine borate, caffeine, and ascorbic acid.

8. A composition for determining the presence of urobilinogen in a test sample, the composition comprising malonyl urea, p-diethylaminobenzaldehyde, sulfosalicylic acid, caffeine, triethanolamine borate and ascorbic acid.

9. A device for determining the presence of urobilinogen in a test sample comprising carrier matrix incorporated with the test composition of any of claims 1–8.

10. A method for determining the presence of urobilinogen in a test sample, said method comprising contacting said sample with the composition of any of claims 1–8 and observing any detectable response.

11. A method for determining the presence of urobilinogen in a test sample, said method comprising contacting said sample with the device of claim 9 and observing any detectable response.

12. A method for preparing a test device for determining the presence of urobilinogen in a test sample comprising incorporating a carrier matrix with the composition of any of claims 1–8.

13. A one-dip method for preparing a test device for determining the presence of urobilinogen in a test sample, the method comprising the steps of
preparing a solution by dissolving in a suitable solvent p-di(lower alkyl)aminobenzaldehyde as an indicator, a buffer substance capable of providing a pH of about 0.5 to 3, and a compound having the structure

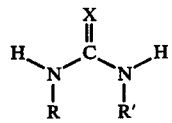

in which X is O or S; and in which R and R', same or different, are lower alkyl, or in which R and R' together are lower alkylene or

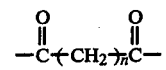

in which n is an integer from 1 to about 6;
contacting a carrier matrix with said solution; and
drying said carrier matrix.

14. The method of claim 13 wherein said compound is one in which R and R' together form

in which n is an integer from 1 to about 6.

15. The method of claim 13 wherein said compound is 2-imidazolidone.

16. The method of claim 13, 14, or 15 wherein said indicator is p-dimethylaminobenzaldehyde.

17. The method of claim 13 wherein said compound is malonyl urea.

18. The method of claim 17 wherein said indicator is p-diethylaminobenzaldehyde.

19. A one-dip method for preparing a test device for determining the presence of urobilinogen in a test sample, said method comprising the steps of
preparing an impregnating solution by dissolving in a suitable solvent, sulfosalicylic acid, p-dimethylaminobenzaldehyde, triethanolamine borate, 2-imidazolidone, caffeine and ascorbic acid;
impregnating a carrier matrix with said solution by immersing said matrix in said solution; and then, after removing it from said solution,
drying said carrier matrix.

20. A one-dip method for preparing a test device for determining the presence of urobilinogen in a test sample, said method comprising the sequential steps of
preparing a solution by dissolving in a suitable solvent sulfosalicylic acid, caffeine, ascorbic acid, triethanolamine borate, p-diethylaminobenzaldehyde, and malonyl urea;
impregnating a carrier matrix with said solution by immersing said matrix in said solution; and
drying said carrier matrix.

* * * * *